(12) United States Patent
Mitome

(10) Patent No.: US 7,733,471 B2
(45) Date of Patent: Jun. 8, 2010

(54) FOREIGN SUBSTANCE INSPECTION APPARATUS

(75) Inventor: Noriyuki Mitome, Shimotsuke (JP)

(73) Assignee: Canon Kabushiki Kaisha, Tokyo (JP)

( * ) Notice: Subject to any disclaimer, the term of this patent is extended or adjusted under 35 U.S.C. 154(b) by 119 days.

(21) Appl. No.: 12/105,194

(22) Filed: Apr. 17, 2008

(65) Prior Publication Data

US 2008/0259319 A1  Oct. 23, 2008

(30) Foreign Application Priority Data

Apr. 20, 2007 (JP) ............................. 2007-111934

(51) Int. Cl.
*G01N 21/00* (2006.01)
(52) U.S. Cl. ................................................ 356/237.1
(58) Field of Classification Search ............... None
See application file for complete search history.

(56) References Cited

U.S. PATENT DOCUMENTS

| | | | |
|---|---|---|---|
| 4,999,510 A | 3/1991 | Hayano et al. | |
| 5,581,348 A | 12/1996 | Miura et al. | |
| 5,585,916 A | 12/1996 | Miura et al. | |
| 5,623,340 A * | 4/1997 | Yamamoto et al. | 356/237.4 |
| 2004/0145734 A1* | 7/2004 | Shibata et al. | 356/237.5 |

FOREIGN PATENT DOCUMENTS

| | | |
|---|---|---|
| JP | 07-005115 A | 1/1995 |
| JP | 07-043312 A | 2/1995 |

* cited by examiner

*Primary Examiner*—Tu T Nguyen
(74) *Attorney, Agent, or Firm*—Canon U.S.A., Inc., IP Division

(57) ABSTRACT

A foreign substance inspection apparatus includes an irradiating unit and first and second detecting units. The irradiating unit is configured to emit irradiating light to be obliquely incident on a surface to be inspected to form a linear irradiation region on the surface to be inspected. The first and second detecting units are arranged on the same side as that provided with the irradiating unit with respect to the surface to be inspected, and they are configured to detect scattered light caused by a foreign substance on the surface to be inspected. The first and second detecting units are arranged at opposite positions with respect to a plane containing the linear irradiation region.

2 Claims, 11 Drawing Sheets

X (SCANNING DIRECTION)

FOREIGN SUBSTANCE INSPECTION APPARATUS

BACKGROUND OF THE INVENTION

1. Field of the Invention

The present invention relates to a foreign substance inspection apparatus.

2. Description of the Related Art

In typical manufacturing processes for manufacturing devices such as semiconductor devices or liquid crystal devices, an exposure apparatus transfers a circuit pattern formed on a reticle onto a resist-coated wafer.

If a foreign substance is present on the reticle in the transfer process, the foreign substance is also transferred onto the wafer. This degrades the yield of device manufacturing.

In particular, when a plurality of shot regions on the wafer are exposed to transfer the circuit pattern by step and repeat, if the foreign substance is present on the reticle, the foreign substance is transferred in all shot regions. This considerably reduces the yield of the device manufacturing.

Hence, it is important to detect the presence of the foreign substance on the reticle in the device manufacturing processes. In many cases, a foreign substance inspection method using a property that the foreign substance isotropically scatters light is employed (see Japanese Patent Laid-Open Nos. 7-43312 and 7-5115).

For example, Japanese Patent Laid-Open No. 7-43312 discloses a technique in which parallel light is obliquely incident on a surface to be inspected of a reticle, and scattered light from a foreign substance is guided to a one-dimensional image sensor by a lens array. The surface to be inspected of the reticle is inspected by forming an image of the foreign substance on the one-dimensional image sensor by the lens array.

FIG. 9A is an illustration showing a basic structure of an optical system of a foreign substance inspection apparatus. In order to simplify the description, only an optical system for foreign substance inspection on a blank surface of a reticle is described. The foreign substance inspection apparatus, however, also has an optical system for foreign substance inspection on a pellicle film. The pellicle film protects a circuit pattern surface of the reticle from a foreign substance. The pellicle film is attached to a reticle 1 using a pellicle frame 2.

An irradiating unit 4 which irradiates the reticle 1 with irradiating light 45 includes a semiconductor laser 41, a collimator lens 42, and a λ/2 plate 43. The collimator lens 42 collimates divergent light emitted from the semiconductor laser 41 to be parallel light. Then, the λ/2 plate 43 polarizes the parallel light to be polarized light having a polarization direction parallel to a plane containing an optical axis of an irradiation optical system and an optical axis of a detection optical system.

The irradiating unit 4 emits the parallel light to be obliquely incident on a blank surface 1a (surface to be inspected) at an angle θ, which is nearly parallel to the blank surface 1a. Accordingly, a linear irradiation region 5 is formed on the blank surface 1a.

If a foreign substance 3 is present in the irradiation region 5, the foreign substance 3 causes scattered light. An imaging lens 71 for receiving scattered light has lens elements arranged in a longitudinal direction of the irradiation region 5. The imaging lens 71 condenses the scattered light on a line sensor 72. The imaging lens 71 forms an image of the irradiation region 5 on the line sensor 72. The imaging lens 71 is constituted by a gradient index lens array. The imaging lens 71 and line sensor 72 are collectively identified as a detecting unit 7.

Referring now also to FIG. 9B, an optical unit 10 including the irradiating unit 4 and the detecting unit 7 of FIG. 9A linearly scans perpendicularly to the longitudinal direction of the irradiation region 5 in a direction along the blank surface 1a, that is, in the X direction, to perform foreign substance inspection for the entire blank surface 1a.

Unfortunately, with the above-described foreign substance inspection apparatus, the irradiating light may enter the reticle from the surface of the blank surface 1a due to refraction. Diffracted light from the circuit pattern may enter the detecting unit 7, and the detecting unit may erroneously detect the diffracted light as the scattered light from the foreign substance.

Referring now also to FIG. 10, light paths causing erroneous detection when viewed from above the reticle and from a measurement surface (X direction) of a side surface 1c of the reticle are illustrated. The irradiating unit 4 forms the linear irradiation region 5 on the blank surface 1a. Since the incident angle to the blank surface 1a is large, a major part (90% or higher of light quantity) of light is reflected, whereas a part of light enters the reticle 1 due to refraction. When the light is refracted at a position P on the blank surface 1a, and is emitted to a line-and-space circuit pattern 102 patterned in the X direction, the circuit pattern 102 produces diffracted light 103L and 103R.

If the light is obliquely emitted to a line-and-space pattern, diffracted light advances in an arrangement direction of the pattern with reference to light specularly reflected by the pattern. Since the light incident on the reticle at an angle nearly parallel to the reticle and refracted is emitted to the pattern, if diffraction with the pattern occurs again when the light enters the reticle at the position P, the diffracted light is totally reflected by the blank surface although it reaches the blank surface.

Similarly to this, although the light totally reflected by the blank surface reaches a region of the pattern surface, if no pattern is present in the region, the light is totally reflected in the region. Also, the total reflection may be caused by a farthermost side surface 1b and a side surface 1c of the reticle 1 depending on the density of the circuit pattern 102.

As described above, the diffracted light 103L may be totally reflected by the pattern surface (of any of a light shielding film portion, a glass portion, and a semitransparent portion), the blank surface, and all the side surfaces of the reticle unless the circuit pattern is irradiated again to cause a diffraction phenomenon. Thus, the light quantity of the diffracted light is not decreased.

Referring to FIG. 10, the diffracted light 103L may return downward (Z direction) in the irradiation region 5 after the total reflection is repeated. If a line-and-space pattern 104 arranged in the Y direction is located at the position, the pattern 104 may cause diffracted light 105, and the detecting unit 7 (illustrated in FIG. 9A) may detect the diffracted light 105. The phenomenon is described below with reference to FIG. 11.

Referring now also to FIG. 11, there is shown a view when FIG. 9A is viewed from the irradiating unit 4. A dotted line plots a light path from the side surface 1c to the pattern 104 of the diffracted light 103L repeating the total reflection. Since the pattern 104 is a line-and-space pattern arranged in the Y direction, the inclination of the diffracted light 105 about the X axis is changed with reference to the specularly reflected light. Accordingly, in FIG. 11, the diffracted light 105 seems to be aligned with the specularly reflected light, however, in FIG. 10, the incident angle of the diffracted light 105 to the blank surface may be smaller than the critical angle, and thus the light may exit to the air. Also, the diffracted light 105 may have an angle close to the optical axis of the imaging lens 71 depending on the density of the circuit pattern 104. The line sensor 72 may detect the light, and erroneously detect it as scattered light from a foreign substance.

The diffracted light 103R also repeats the total reflection similarly to the diffracted light 103L. When the diffracted light 103R is reflected by the side surface 1b of the reticle and enters a circuit pattern region 101, the diffracted light 103R gradually disappears because diffracted light is produced in the circuit pattern region. The produced diffracted light would not enter the detecting unit 7, thereby not causing erroneous detection.

SUMMARY OF THE INVENTION

The present invention provides a foreign substance inspection apparatus capable of reducing erroneous detection due to diffracted light from a pattern and providing highly accurate foreign substance inspection.

According to an aspect of the present invention, a foreign substance inspection apparatus includes an irradiating unit and first and second detecting units. The irradiating unit is configured to emit irradiating light to be obliquely incident on a surface to be inspected to form a linear irradiation region on the surface to be inspected. The first and second detecting units are arranged on the same side as that provided with the irradiating unit with respect to the surface to be inspected, the first and second detecting units configured to detect scattered light caused by a foreign substance on the surface to be inspected. Further, the first and second detecting units are arranged at opposite positions with respect to a plane containing the linear irradiation region.

Further features and aspects of the present invention will become apparent from the following description of exemplary embodiments with reference to the attached drawings.

DESCRIPTION OF THE EMBODIMENTS

Embodiments of the present invention are described below with reference to the attached drawings.

First Embodiment

Figure 1A:
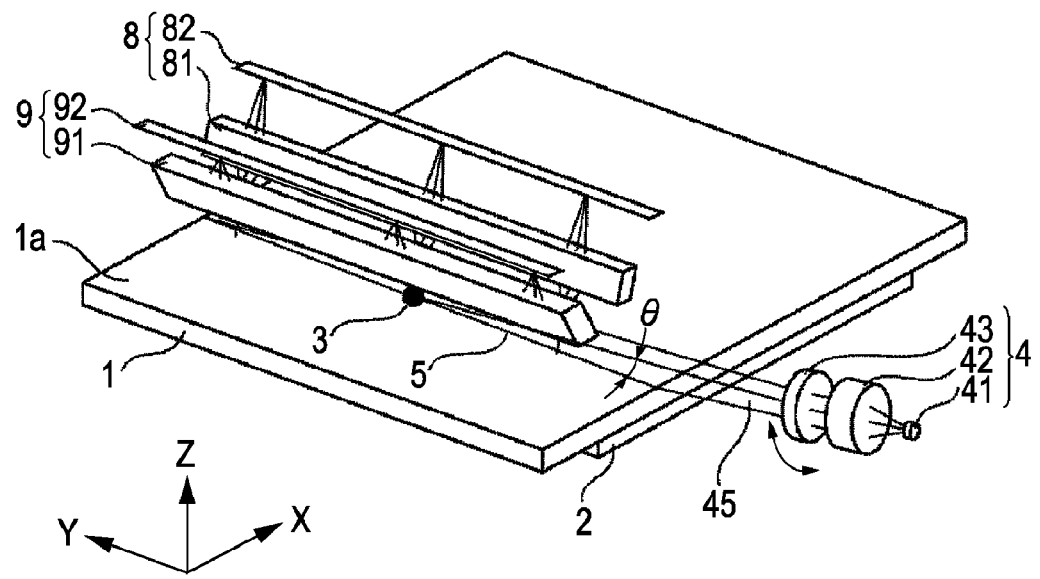
FIG. 1A is a view schematically showing a foreign substance inspection apparatus according to a first embodiment of the present invention.
Figure 1B:
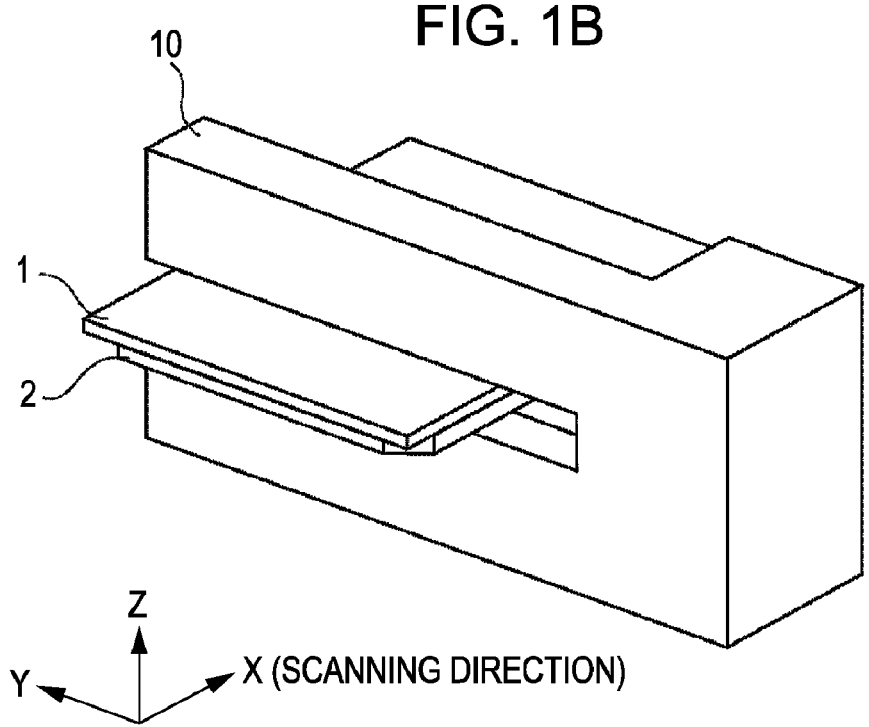
FIG. 1B is a view schematically showing the foreign substance inspection apparatus according to the first embodiment.

FIGS. 1A and 1B illustrate a foreign substance inspection apparatus according to a first embodiment of the present invention.

FIG. 1A is an illustration showing a basic structure of the foreign substance inspection apparatus according to the first embodiment. In order to simplify the description, described herein is only an optical system for foreign substance inspection on a blank surface of a reticle. The foreign substance inspection apparatus, however, also has an optical system for foreign substance inspection on a pellicle film of the reticle. The pellicle film is attached to a reticle 1 using a pellicle frame 2.

Figure 9A:
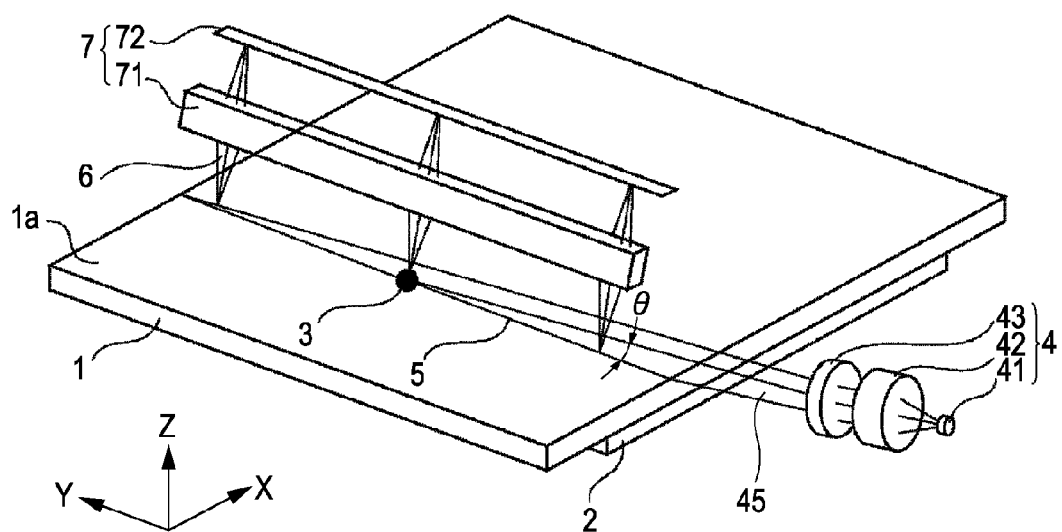
FIG. 9A is a view schematically showing a foreign substance inspection apparatus according to prior art.
Figure 9B:
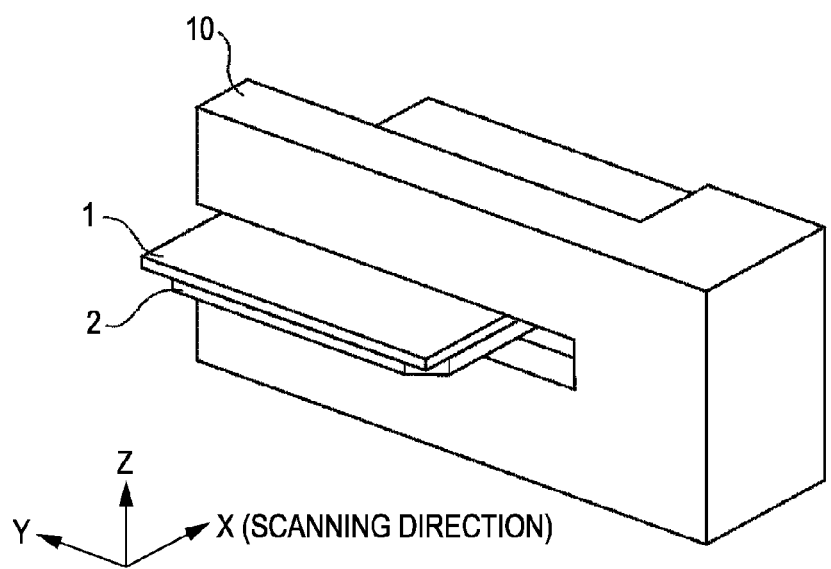
FIG. 9B is a view schematically showing the foreign substance inspection apparatus according to prior art.
Figure 10:
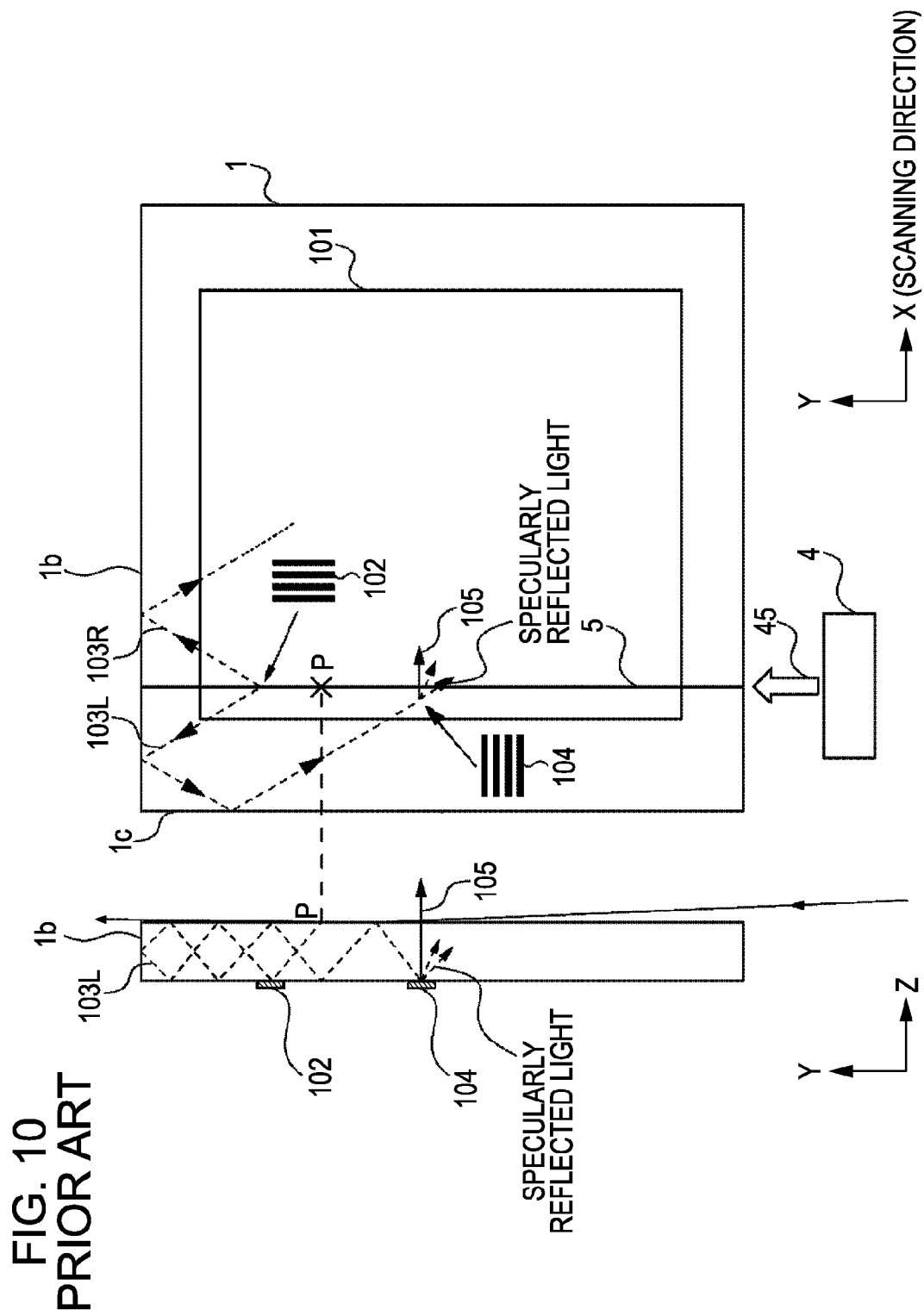
FIG. 10 is a view schematically showing a problem with the foreign substance inspection apparatus according to prior art.
Figure 11:
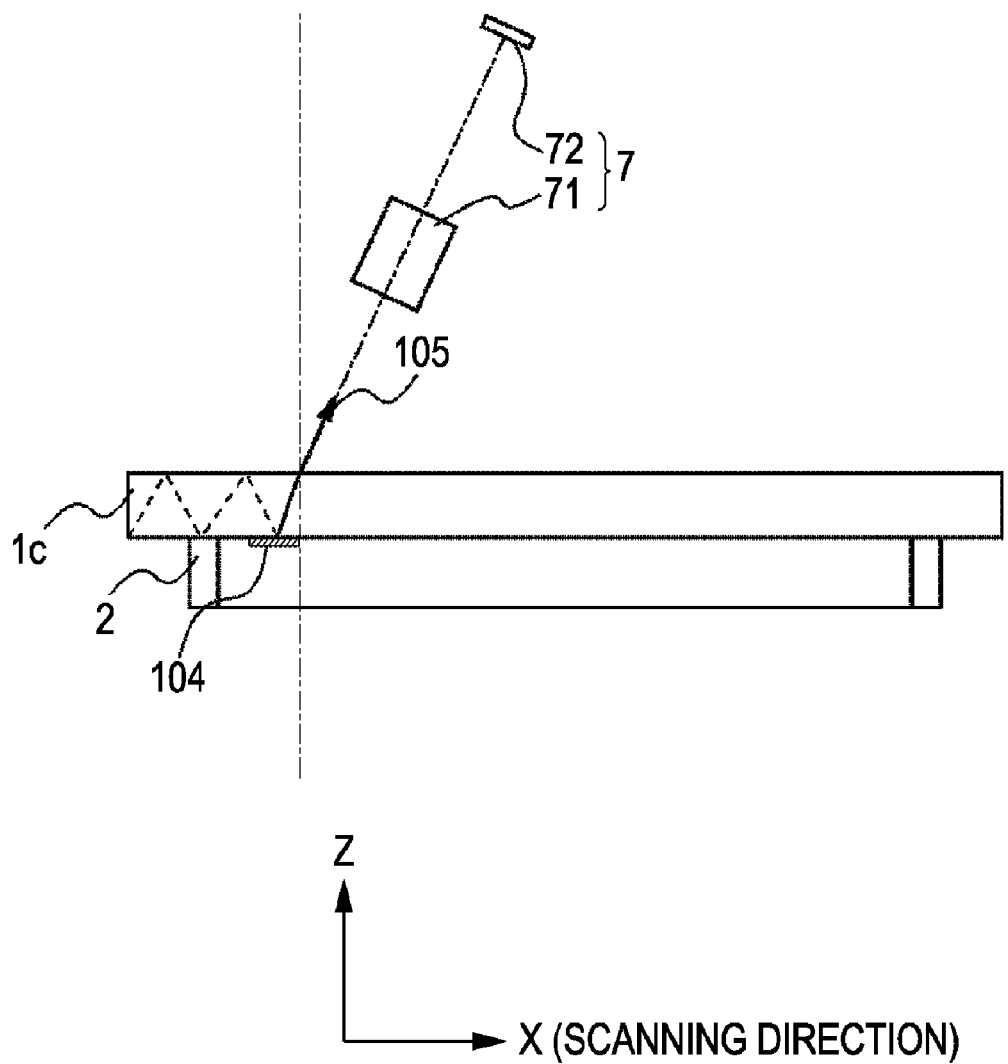
FIG. 11 is a cross section showing the problem of the foreign substance inspection apparatus according to prior art.

An irradiating unit 4 includes similarly to the configuration in FIG. 9A a semiconductor laser 41 as a light source, a collimator lens 42, and a $\lambda/2$ plate 43 as a wave plate. The $\lambda/2$ plate 43 is rotatable around the optical axis of the irradiating unit 4 and is driven by a driving mechanism (not shown). The detailed function thereof will be described later. The irradiating unit 4 irradiates the reticle 1 with irradiating light 45 which is linearly polarized light.

A first detecting unit 8 has a configuration similar to that of the detecting unit 7 in FIG. 9A, and more particularly includes an imaging lens 81 and a line sensor 82. In this embodiment, a second detecting unit 9 is additionally arranged opposite to the first detecting unit 8 with respect to an incident surface of the irradiating light 45 from the irradiating unit 4 (i.e., a plane containing a wave normal to the irradiating light 45 and a normal to a surface to be inspected at an incident point, or a plane containing the linear irradiation region 5). The second detecting unit 9 has a configuration similar to that of the detecting unit 7 in FIG. 9A, and more particularly includes an imaging lens 91 and a line sensor 92. For purposes of demonstrating features of the embodiment, a foreign substance 3 is shown in the irradiation region 5.

Referring now also to FIG. 1B, an optical unit 10 linearly scans perpendicularly to a longitudinal direction of the irradiation region 5 in a direction along a blank surface 1a, that is, in the X direction, to perform foreign substance inspection for the entire blank surface 1a. The optical unit 10 includes the irradiating unit 4 and the first and second detecting units 8 and 9 of FIG. 1A, these units 4, 8, and 9 being integrally arranged. The positions of the reticle 1 and pellicle frame 2 relative to the optical unit 10 are also shown.

Figure 2:
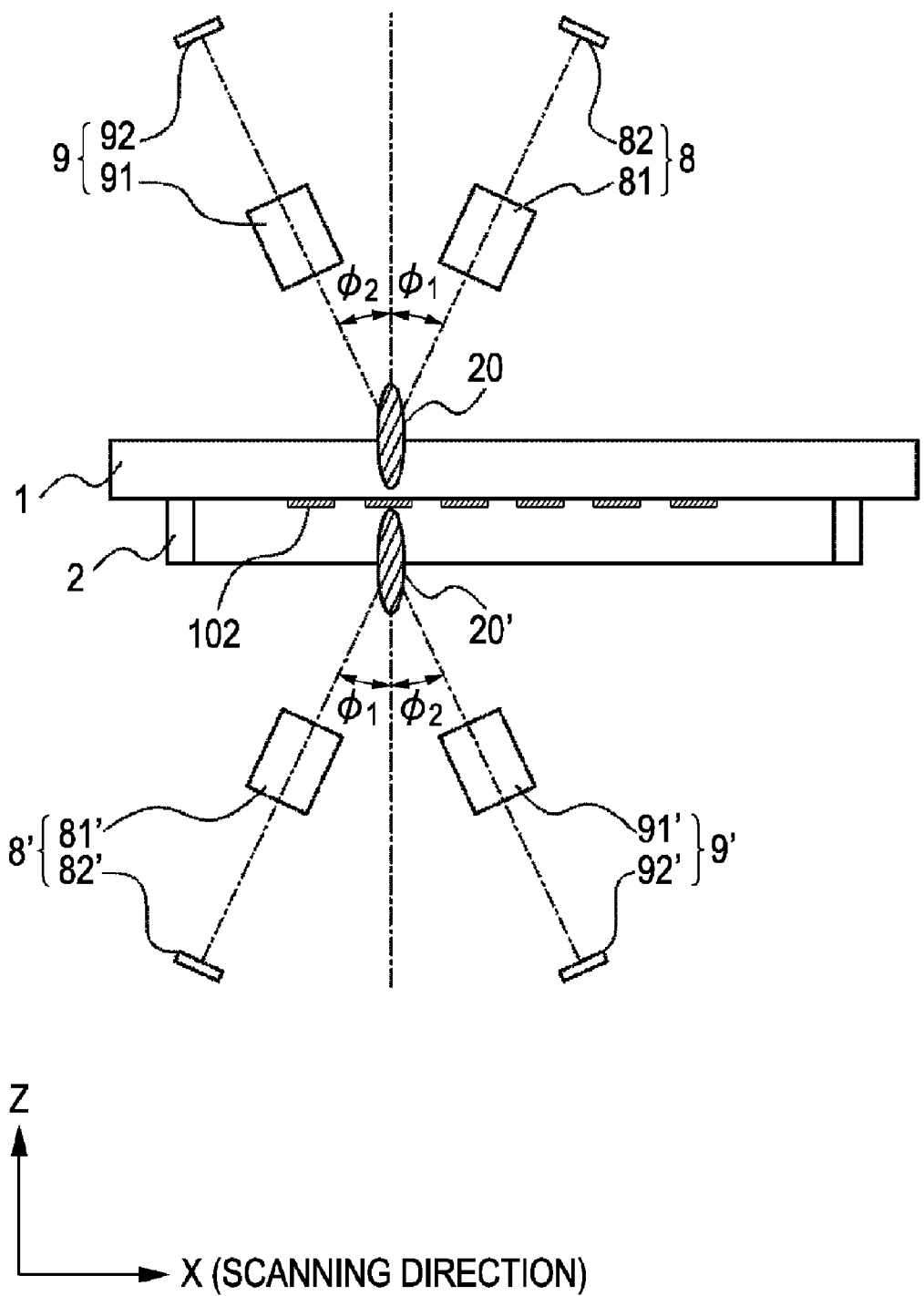
FIG. 2 is a cross section showing the foreign substance inspection apparatus according to the first embodiment.

Referring now also to FIG. 2, an illustration showing a basic structure of an entire detecting unit and setting of polarization directions (polarizing axis directions) of laser beams is provided, viewed in an incident direction of the beams to the reticle, that is, in the Y direction. Reference numerals 20 and 20' in the drawing respectively denote a cross section of the irradiating light at the blank surface and a cross section of the irradiating light at the pellicle surface. Oblique lines in the cross sections represent the polarizing directions of the irradiating light. The optical axes of imaging lenses 81 and 81' for receiving light are inclined at an angle $\phi_1$ with respect to a normal to the surface to be inspected (blank surface or pellicle surface). The optical axes of imaging lenses 91 and 91' for receiving light are inclined at an angle $\phi_2$ with respect to the normal to the surface to be inspected (blank surface or pellicle surface). A line-and-space pattern 102 is also shown.

When the line sensors 82 and 82' of the detecting units 8 and 8' receive light, the polarization direction of the irradiating light is set parallel to the optical axes of the detecting units 8 and 8' to be aligned with oblique lines in FIG. 2. When the line sensors 92 and 92' of the detecting units 9 and 9' receive light, though not shown, the $\lambda/2$ plate (changing part) 43 is rotated so that the polarization direction becomes parallel to the optical axes of the detecting units 9 and 9'. By changing the polarization direction depending on the detection unit to be used, it is possible to increase the intensity of the scattered light if the particle size increases.

Figure 3:
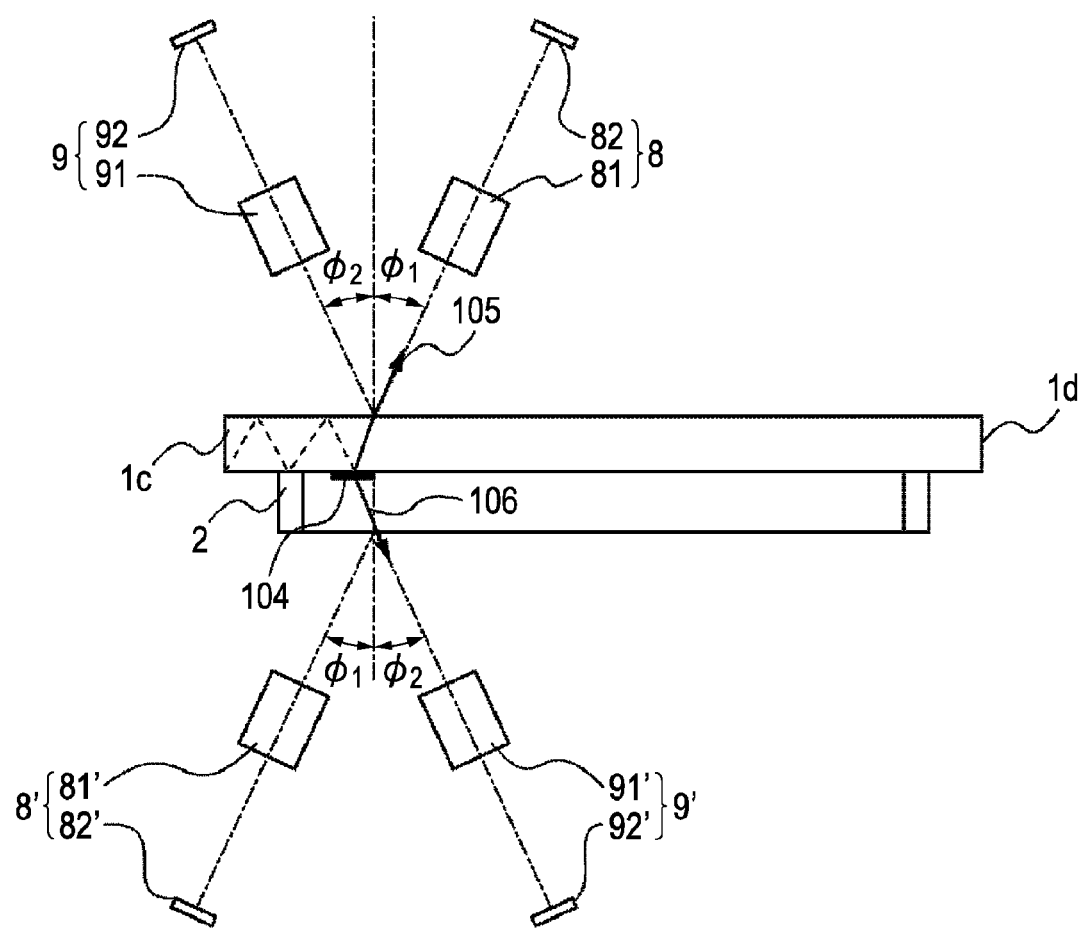
FIG. 3 is a cross section showing the foreign substance inspection apparatus according to the first embodiment.
Figure 3:

Referring now also to FIG. 3, reasons for providing the two detecting units for the blank surface and the pellicle surface are described. Similarly to FIG. 2, FIG. 3 is viewed in the incident direction of the beam to the reticle, that is, in the Y direction. The detecting unit 8 may detect the diffracted light 105 as described in FIG. 12, however, the detecting unit 9 hardly detects the diffracted light 105.

For the detection of the pellicle surface, the detecting unit 9' may detect the diffracted light 106, however, the detecting unit 8' hardly detects the diffracted light 106. The detecting unit which obliquely faces a side surface 1c or 1d of the reticle likely provides erroneous detection for the position of the irradiation region 5 because of an effect of the diffracted light from the pattern.

In this embodiment, since the two (first and second) detecting units are provided for each of the blank surface and the pellicle surface, one of the two (first and second) detecting units less likely results in the erroneous detection because of the diffracted light from the pattern. Accordingly, the foreign substance inspection apparatus of this embodiment can highly accurately inspect a foreign substance.

In order that the detecting units 8 and 9 (or 8' and 9') detect an equivalent intensity of scattered light from the foreign substance, their light receiving angles may be set as $\phi_1=\phi_2$, however, the light receiving angles need not be equivalent.

Figure 4:
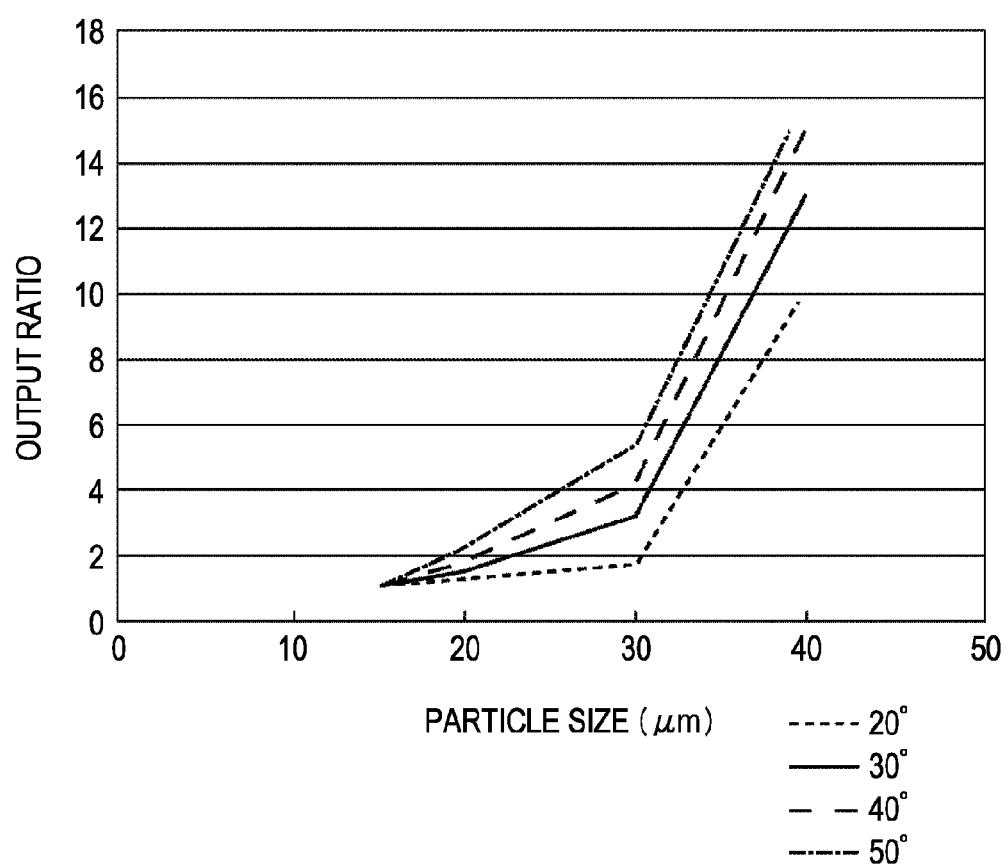
FIG. 4 is a graph showing the relationship between a particle size and an output of a scattered light sensor, depending on a light receiving angle.

FIG. 4 is data showing the relationship between a particle size and an output of the intensity of scattered light with the condition of the light receiving angle varied. It is assumed that the intensity of scattered light is 1 when the particle size is 15 µm with any condition of the light receiving angle. The intensity of scattered light increases as the particle size increases with any light receiving angle of 20°, 30°, 40°, and 50°. Accordingly, the particle size can be determined.

Figure 5:
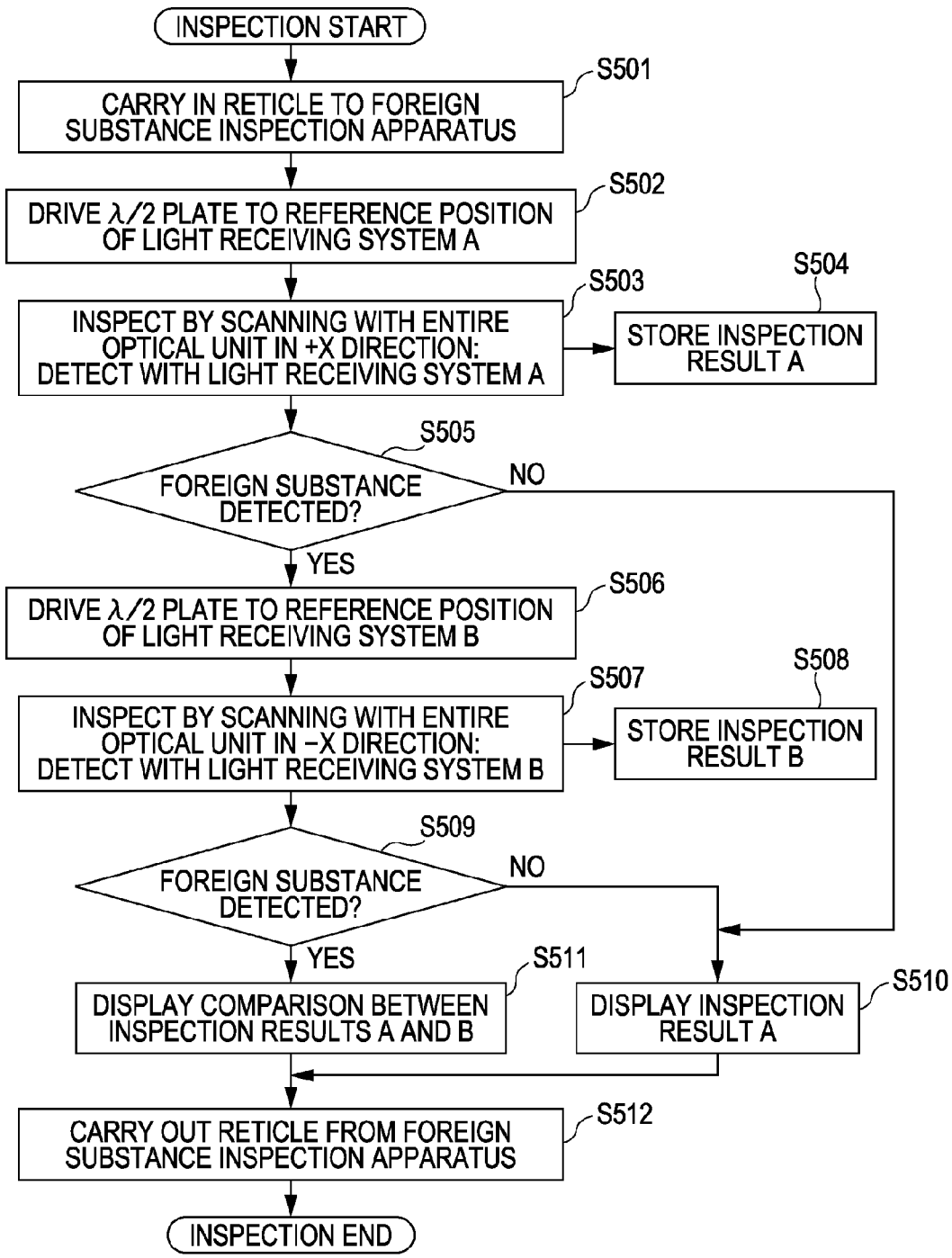
FIG. 5 is a flowchart showing a foreign substance inspection method according to the first embodiment.

FIG. 5 is a flowchart for the inspection with the two detecting units by moving the optical unit 10 relative to the reticle 1. In step S501, the reticle is carried into the foreign substance inspection apparatus. In step S502, the $\lambda/2$ plate 43 is driven to a reference position for the first detecting unit 8 (light receiving system A). In step S503, the optical unit 10 inspects the reticle 1 by scanning the reticle 1 in the +X direction (first direction). The first detecting unit 8 (light receiving system A) receives the scattered light from a foreign substance on the reticle and the received light is inspected. A first inspection result (RESULT A) is generated and in step S504 stored in a memory in the foreign substance inspection apparatus. In step S505, a determination is made whether the inspection result (RESULT A) indicates that a foreign substance is detected. If no foreign substance is detected (NO in step S505), then the inspection result (RESULT A) is displayed in step S510, the reticle is carried out of the foreign substance inspection apparatus in step S512, and the inspection is ended. If a foreign substance is detected (YES in step S505), then processing continues in step S506. In step S506, the $\lambda/2$ plate 43 is driven to a reference position of the second detecting unit 9 (light receiving system B). In step S507, the optical unit 10 inspects the reticle 1 by scanning the reticle 1 in the −X direction (second direction) which is opposite to the +X direction. The $\lambda/2$ plate 43 is rotated as described above when the scanning direction is changed. The second detecting unit 9 (light receiving system B) receives the scattered light from a foreign substance on the reticle and the received light is inspected. A second inspection result (RESULT B) is generated and in step S508 stored in a memory in the foreign substance inspection apparatus. In step S509, a determination is made whether the inspection result (RESULT B) indicates that a foreign substance is detected. If no foreign substance is detected (NO in step S509), then the inspection result (RESULT B) is displayed in step S510, the reticle is carried out of the foreign substance inspection apparatus in step S512, and the inspection is ended. If a foreign substance is detected (YES in step S509), then processing continues in step S511. In step S511, first and second inspection results (RESULT A and RESULT B) of the detecting units 8 and 9 respectively are obtained. In this embodiment, the two inspection results (RESULT A and RESULT B) indicate the detected particle sizes in each result for each coordinate of 1 mm$^2$ on the surface to be inspected. The two inspection results (RESULT A and RESULT B) are compared for each coordinate, and one of the inspection results representing a smaller detected particle size is determined as a final inspection result. In step S511, comparison and final inspection are displayed on a display device (not shown). A conventional display device, such as a monitor, may be used for this purpose. In the case of the erroneous detection due to the pattern, only one of the detecting units typically detects the scattered light which indicates the presence of the foreign substance, and thus, the erroneous result typically is deleted. In the case of the detection of the foreign substance, the two detecting units detect an equivalent particle size, thus the comparison provides for correct detection of the foreign substance. With the inspection by the method, the erroneous detection due to the diffracted light from the pattern can be prevented, and the foreign substance can be correctly detected. After step S511, processing continues in step S512 as described above, and the processing is ended.

Second Embodiment

Figure 6A:
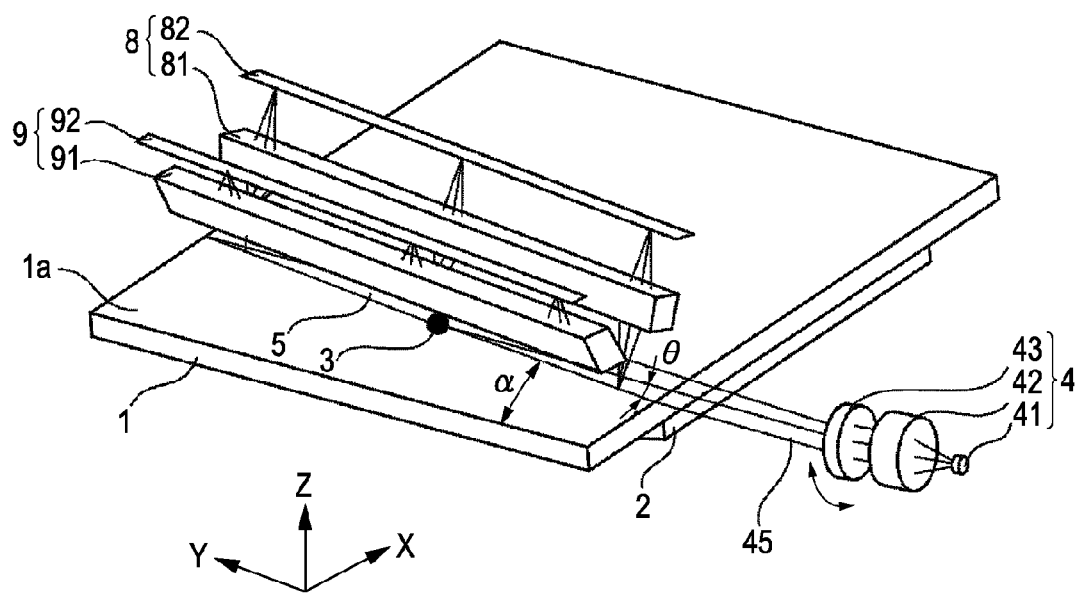
FIG. 6A is a view schematically showing a foreign substance inspection apparatus according to a second embodiment of the present invention.
Figure 6B:
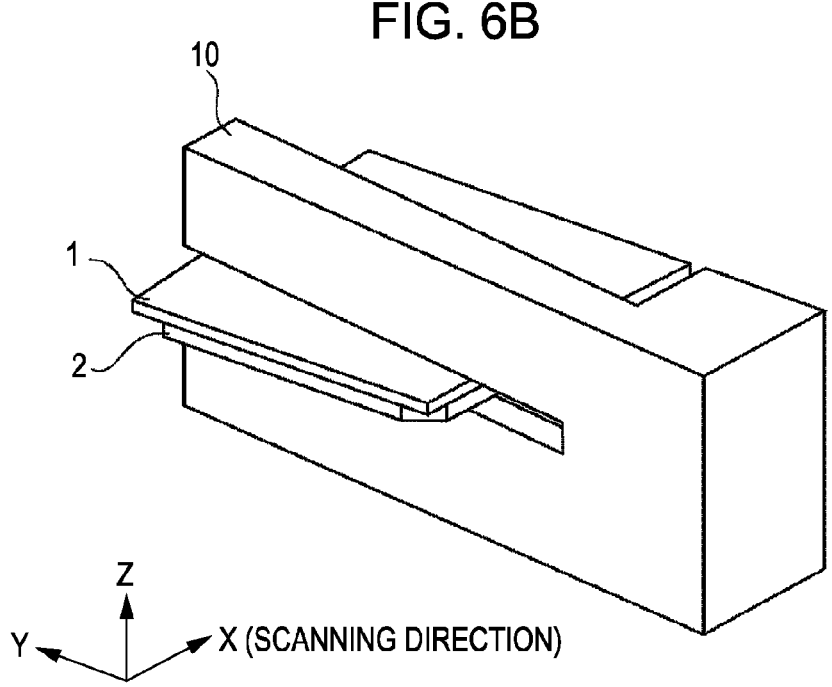
FIG. 6B is a view schematically showing the foreign substance inspection apparatus according to the second embodiment.

FIGS. 6A and 6B illustrate a foreign substance inspection apparatus according to a second embodiment.

This embodiment differs from the first embodiment in that the optical unit 10 is inclined at an angle α in the X-Y plane, with respect to the reticle 1. A scanning direction of the inspection for the entire reticle surface is parallel to or perpendicular to the side surface of the reticle 1.

Figure 7:
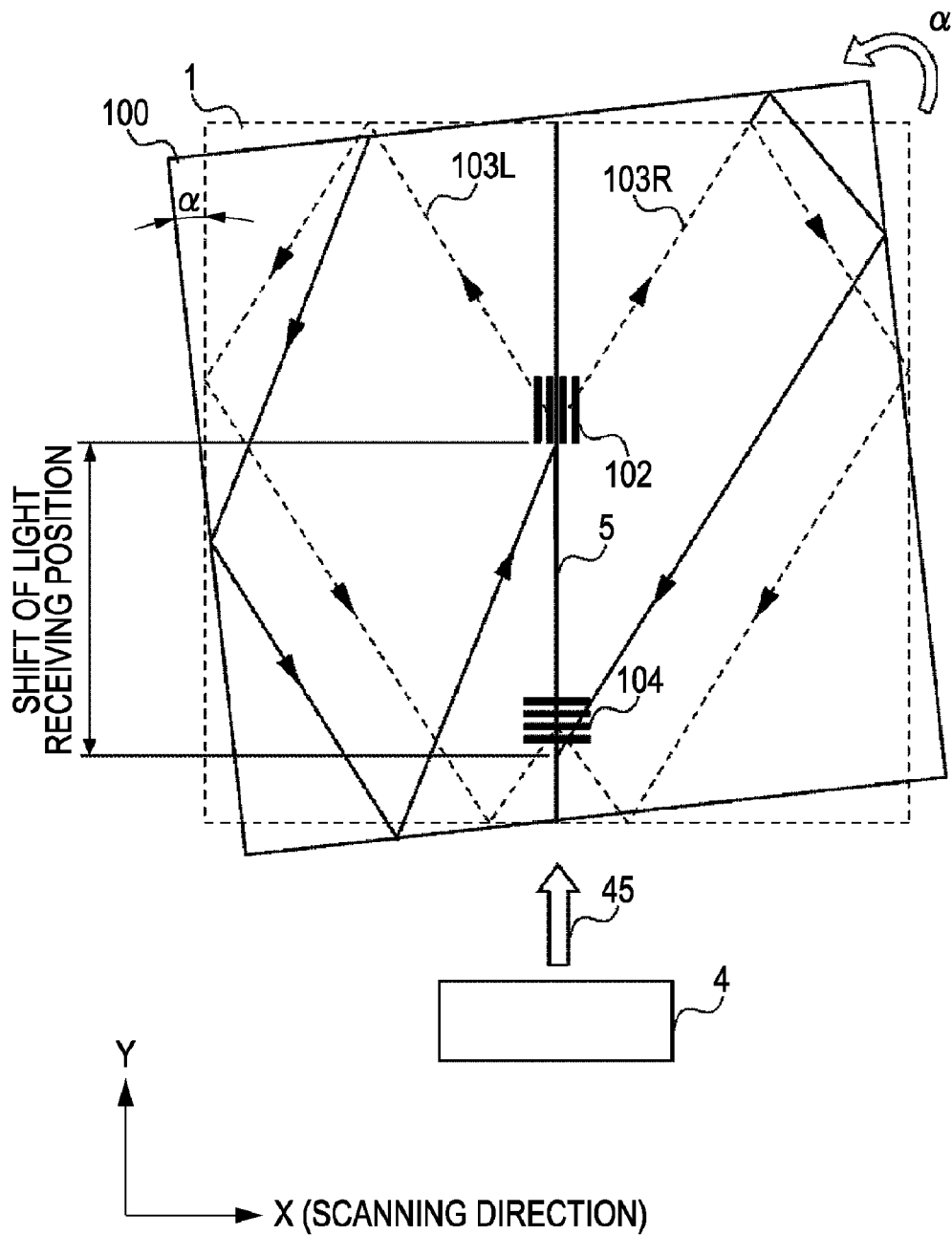
FIG. 7 is an illustration showing a light path of diffracted light in a reticle.

FIG. 7 is viewed from above the reticle to show that the irradiation region 5 is located at the center of the reticle in the X direction. In FIG. 7, the reticle of the second embodiment is referenced as reticle 100. With reference to the position of the optical system, a reticle 100 of the second embodiment is rotated in a counterclockwise (CCW) direction at an angle α in comparison with the reticle 1 of the first embodiment.

The lines with arrowheads plotted inside the reticle 100 define light paths of diffracted light 103L and 103R in the reticle 100 caused by the circuit pattern 102.

Light paths indicated by dotted lines are of the first embodiment 1. The diffracted light 103L and the diffracted light 103R are repeatedly reflected in the reticle 1. Their light paths are symmetric, and hence, the diffracted light 103L and the diffracted light 103R return downward (Z direction) in the irradiation region 5 to the same position in the Y direction. Then, the detecting units 8 and 9 detect the diffracted light with the same coordinate, thereby possibly erroneously detecting the diffracted light.

In contrast, the light paths indicated by the solid lines are of the second embodiment. The diffracted light 103 and the diffracted light 103R are repeatedly reflected in the reticle 100, and return downward (Z direction) in the irradiation region 5. The light paths are asymmetric, and hence, the returning positions are different in the Y direction. Accordingly, even when the circuit pattern 104 causing diffracted light is located at this position, the light receiving positions with the first and second detecting units 8 and 9 are different. The inspection result with a smaller output is selected, thereby preventing the erroneous detection.

In the second embodiment, however, the scanning stroke may become large, and the inspection may need an additional time. This will be described with reference to FIG. 8.

Figure 8:
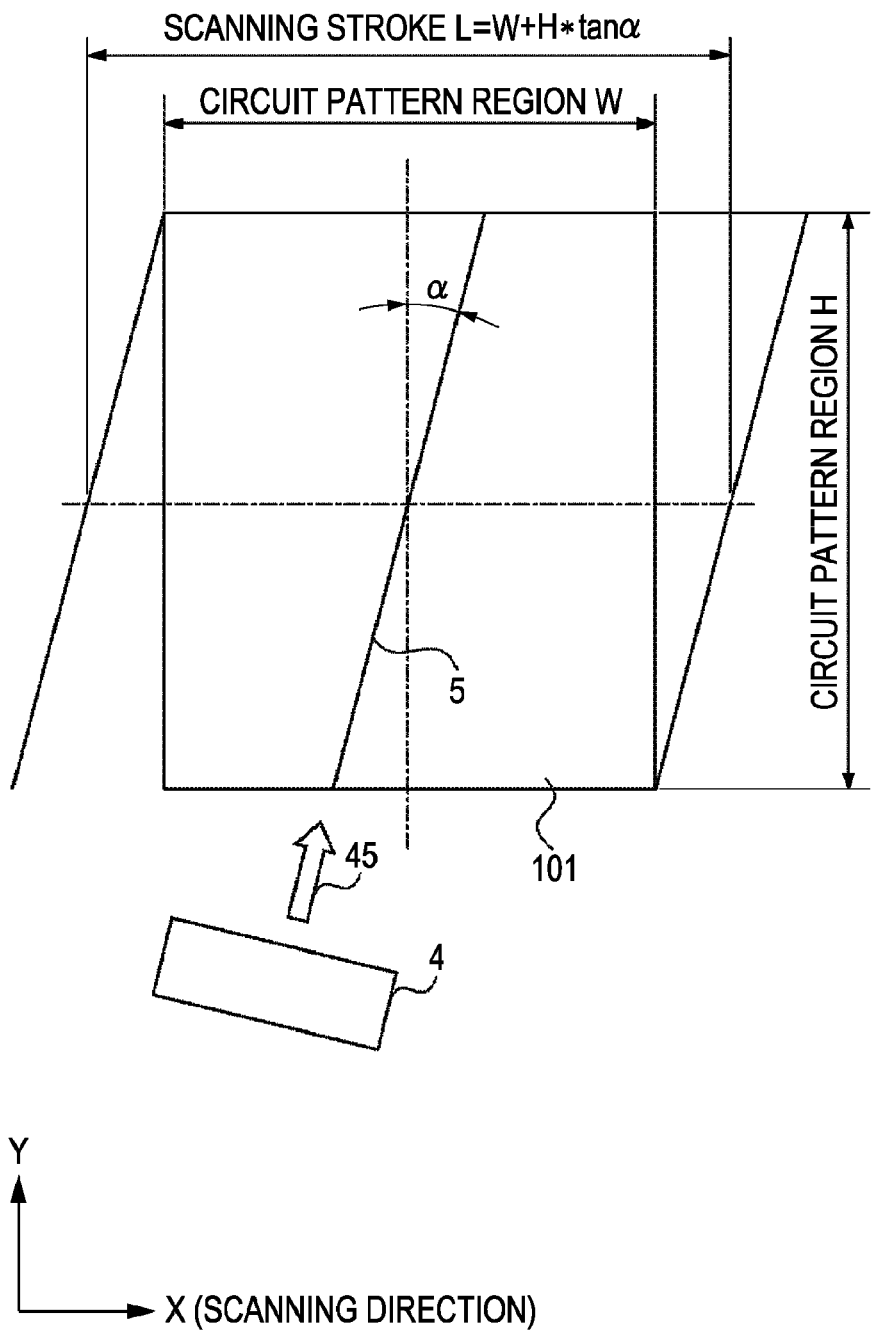
FIG. 8 is a view schematically showing a scanning stroke of the foreign substance inspection apparatus according to the second embodiment.

FIG. 8 shows a circuit pattern region 101 viewed from above the reticle. The circuit pattern region has a length W in the X direction and a length H in the Y direction. This is a region to be inspected. When the irradiation region 5 with the irradiating unit 4 extends in the Y direction, a scanning stroke of a related art is W. In contrast, the irradiation region 5 of the second embodiment is inclined with respect to the circuit pattern region 101 at an angle α. Accordingly, the scanning stroke of this embodiment is W+H*tan α, which is larger than the circuit pattern region W. This may take an additional time.

With this embodiment, although the inspection needs an additional time, the erroneous detection of the diffracted light from the pattern with the first and second detecting units 8 and 9 can be reduced, thereby a foreign substance can be inspected further highly accurately, in comparison with the first embodiment.

With the above embodiments, a foreign substance can be highly accurately inspected by the foreign substance inspection apparatus without erroneously detecting the diffracted light caused by the pattern.

In the above embodiments, while the description has focused on the foreign substance inspection apparatus for foreign substance inspection on the surface (blank surface, pellicle film) of the reticle, the present invention may be applied to a foreign substance inspection apparatus for foreign substance inspection on the surface of a transparent substrate having a pattern, instead of the reticle.

Also, in the above embodiments, the linear irradiation region is formed on the surface of the reticle by emitting a light beam having a linear cross section on the surface of the reticle. However, it is not limited thereto. For example, an apparatus for detecting foreign particles is disclosed in U.S. Pat. No. 4,999,510, in which a light beam having a spot cross section may be incident on a surface of a reticle, and the light beam may scan by way of a galvano-mirror, whereby a linear irradiation region is formed on the surface of the reticle.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Application No. 2007-111934 filed Apr. 20, 2007, which is hereby incorporated by reference herein in its entirety.

What is claimed is:

1. A foreign substance inspection apparatus comprising:
    an irradiating unit configured to emit irradiating light to be obliquely incident on a surface to be inspected to form a linear irradiation region on the surface to be inspected; and
    first and second detecting units arranged on a same side as that provided with the irradiating unit with respect to the surface to be inspected, the first and second detecting units configured to detect scattered light caused by a foreign substance on the surface to be inspected,
    wherein the first and second detecting units are arranged at opposite positions with respect to a plane containing the linear irradiation region,
    wherein the irradiating unit emits linearly polarized light as the irradiating light to be incident on the surface to be inspected,
    wherein the irradiating unit has a changing part configured to change a polarization direction of the linearly polarized light to be incident on the surface to be inspected,
    wherein the first and second detecting units are selectively used so that one is used at a time, and
    wherein the changing part changes the polarization direction of the linearly polarized light in accordance with the detecting unit that is used.

2. The foreign substance inspection apparatus according to claim 1,
    wherein, to scan the surface to be inspected with irradiating light, the irradiating unit, the first detecting unit, and the second detecting unit are integrally arranged and moved in a first direction and a second direction opposite to the first direction relative to the surface to be inspected,
    wherein the first detecting unit detects the scattered light when scanning in the first direction,
    wherein the second detecting unit detects the scattered light when scanning in the second direction, and
    wherein the polarization direction of the linearly polarized light to be incident on the surface to be inspected is changed between the scanning in the first direction and the scanning in the second direction.

* * * * *